United States Patent
Page (10) Patent No.: US 12,193,960 B1
(45) Date of Patent: Jan. 14, 2025

(54) FINGER STRAIGHTENING DEVICE

(71) Applicant: Andrew Page, Vidalia, GA (US)

(72) Inventor: Andrew Page, Vidalia, GA (US)

( * ) Notice: Subject to any disclaimer, the term of this patent is extended or adjusted under 35 U.S.C. 154(b) by 321 days.

(21) Appl. No.: 17/942,210

(22) Filed: Sep. 12, 2022

Related U.S. Application Data (60) Provisional application No. 63/252,717, filed on Oct. 6, 2021.

(51) Int. Cl.
*A61F 5/10* (2006.01)

(52) U.S. Cl.
CPC ..................... *A61F 5/10* (2013.01)

(58) Field of Classification Search
CPC ..... A61F 5/10; A61F 5/05866; A61F 5/05858
See application file for complete search history.

(56) References Cited

U.S. PATENT DOCUMENTS

| | | | |
|---|---|---|---|
| 1,174,887 A * | 3/1916 | Meriwether | A61F 13/105 |
| | | | 16/241 |
| 2,548,378 A | 4/1951 | Kleinfield | |
| 3,794,019 A * | 2/1974 | Ritland | A61F 5/10 |
| | | | 602/22 |
| 4,167,044 A * | 9/1979 | Girard | A61F 2/72 |
| | | | 623/64 |
| 4,644,941 A | 2/1987 | Ogle, II | |
| 4,657,000 A | 4/1987 | Hepburn | |
| 5,183,458 A * | 2/1993 | Marx | A61F 5/10 |
| | | | 602/30 |
| 5,230,699 A * | 7/1993 | Grasinger | A61F 5/05866 |
| | | | 128/880 |
| 5,232,436 A * | 8/1993 | Janevski | A61F 5/013 |
| | | | 602/22 |
| 5,787,896 A * | 8/1998 | Sackett | A41D 19/01588 |
| | | | 128/880 |
| 5,848,983 A * | 12/1998 | Basaj | A61F 5/05866 |
| | | | 602/5 |
| 5,947,915 A | 9/1999 | Thibodo, Jr. | |
| 6,575,925 B1 | 6/2003 | Noble | |
| 6,692,452 B2 | 2/2004 | Chow | |

(Continued)

FOREIGN PATENT DOCUMENTS

| | | |
|---|---|---|
| CN | 206026514 U | 3/2017 |
| JP | 3086716 U | 7/2002 |

(Continued)

*Primary Examiner* — Camtu T Nguyen
(74) *Attorney, Agent, or Firm* — John Rizvi; John Rizvi, P.A.—The Patent Professor®

(57) ABSTRACT

A finger straightening device includes a base and a cover which may be coupled to the base. The base includes a top surface for a user to rest a finger thereon. The cover includes an inner surface for applying a force on a finger of a user. The base and the cover define a cavity therebetween, and the inner surface of the cover applies the force on a finger inserted in the cavity and resting on the top surface of the base. The finger straightening device further includes a first securing element for adjustably coupling the base and the cover at a distal portion and a second securing element for adjustably coupling the base and the cover at a central portion of the finger straightening device. The finger straightening device further includes a fastener for engagement with the second securing element so as to define the force being applied to the finger inserted in the cavity.

20 Claims, 7 Drawing Sheets

(56) References Cited

U.S. PATENT DOCUMENTS

| | | |
|---|---|---|
| 2009/0204044 A1 | 8/2009 | Benison |
| 2010/0004576 A1 | 1/2010 | Molnar |
| 2014/0267116 A1 | 9/2014 | Weiner |

FOREIGN PATENT DOCUMENTS

| | | |
|---|---|---|
| JP | 3095817 U | 8/2003 |
| KR | 20140030590 A | 3/2014 |

\* cited by examiner

FINGER STRAIGHTENING DEVICE

CROSS-REFERENCE TO RELATED APPLICATION

This application claims the benefit of U.S. Provisional Patent Application No. 63/252,717, filed on Oct. 6, 2021, which is incorporated by reference herein in its entirety.

FIELD OF THE INVENTION

The present invention relates generally to devices for supporting a finger of a user, and more particularly to a device that allows a user to straighten a finger by applying pressure thereto.

BACKGROUND OF THE INVENTION

Generally, individuals who have crooked or bent fingers due to accidents, dislocations, and/or surgeries have to deal with discomfort and pain in the fingers. Such individuals have to straighten their fingers from time to time on order to relieve pain from the fingers and relax the muscles and tendons surrounding the fingers. Conventionally available devices for such a purpose are not convenient for use by an individual since such devices are complicated to use and cause discomfort to the individuals during their use.

Accordingly, there is need for a solution to at least one of the aforementioned problems. For instance, there is an established need for a finger straightening device that is convenient for an individual to use. Further, there is an established need for a finger straightening device that can be used by an individual to apply a predetermined pressure on their fingers so as to straighten the fingers Further, there is an established need for a finger straightening device that allows the individual to easily vary the pressure that need to be applied on the finger based on the pain being experienced by the individual.

SUMMARY OF THE INVENTION

The present invention relates to a finger straightening device comprising a base and a cover configured to be coupled to the base. The base and the cover define a cavity therebetween for insertion of a finger of a user. An inner surface of the cover is configured to apply a predetermined force on a finger inserted in the cavity and resting on a top surface of the base. The finger straightening device comprises a first securing element and a second securing element for adjustably coupling the base and the cover at a distal portion and at a central portion of the finger straightening device respectively. The finger straightening device may be selectively adjusted to define the force being applied to a finger inserted in the cavity.

In an aspect, the base may include a first aperture, and the cover may include a through hole for facilitating coupling of the base and the cover via the first securing element.

In an aspect, the base may include a second aperture and a third aperture for facilitating coupling of the base and the cover via the second securing element.

In an aspect, the second securing element may include a U-shaped bracket having a first leg and a second leg configured to pass through the second aperture and the third aperture respectively, and the fastener may include a pair of fasteners for engaging with a corresponding one of the first leg and the second leg of the second securing element.

In an aspect, the first securing element may be a single element having a first curved end and a second curved end.

In another aspect, the first securing element may include a threaded bolt and a cup nut.

These and other objects, features, and advantages of the present invention will become more readily apparent from the attached drawings and the detailed description of the embodiments and examples, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other embodiments. All of the embodiments described below are exemplary embodiments provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in the drawings. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In the following description, certain specific details are set forth in order to provide a thorough understanding of various disclosed embodiments. However, one skilled in the relevant art will recognize that embodiments may be practiced without one or more of these specific details, or with other methods, components, materials, and the like. In other instances, well-known elements associated with vending devices have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

It should be noted that throughout the specification and claims which follow, the term "finger" is not limited to any specific finger of a user, rather, the term "finger" intends to cover all the fingers of an individual.

It should also be noted that throughout the specification and claims which follow, the application of the device is not limited to only the fingers of a user. The device of the present invention can be used for an injured or recovering limb of a user, such as toes.

As used in this specification and the appended claims, the singular forms "a," "an," and "the" include plural referents unless the content clearly dictates otherwise, and the vice versa. It should also be noted that the term "or" is generally employed in its broadest sense, that is, as meaning "and/or" unless the content clearly dictates otherwise.

The headings and Abstract of the Disclosure provided herein are for convenience only and do not interpret the scope or meaning of the embodiments.

Shown throughout the drawings, the present invention is directed toward a finger straightening device that allows users to straighten their fingers, thus relieving users of pain and providing comfort to the users.

Figure 1:
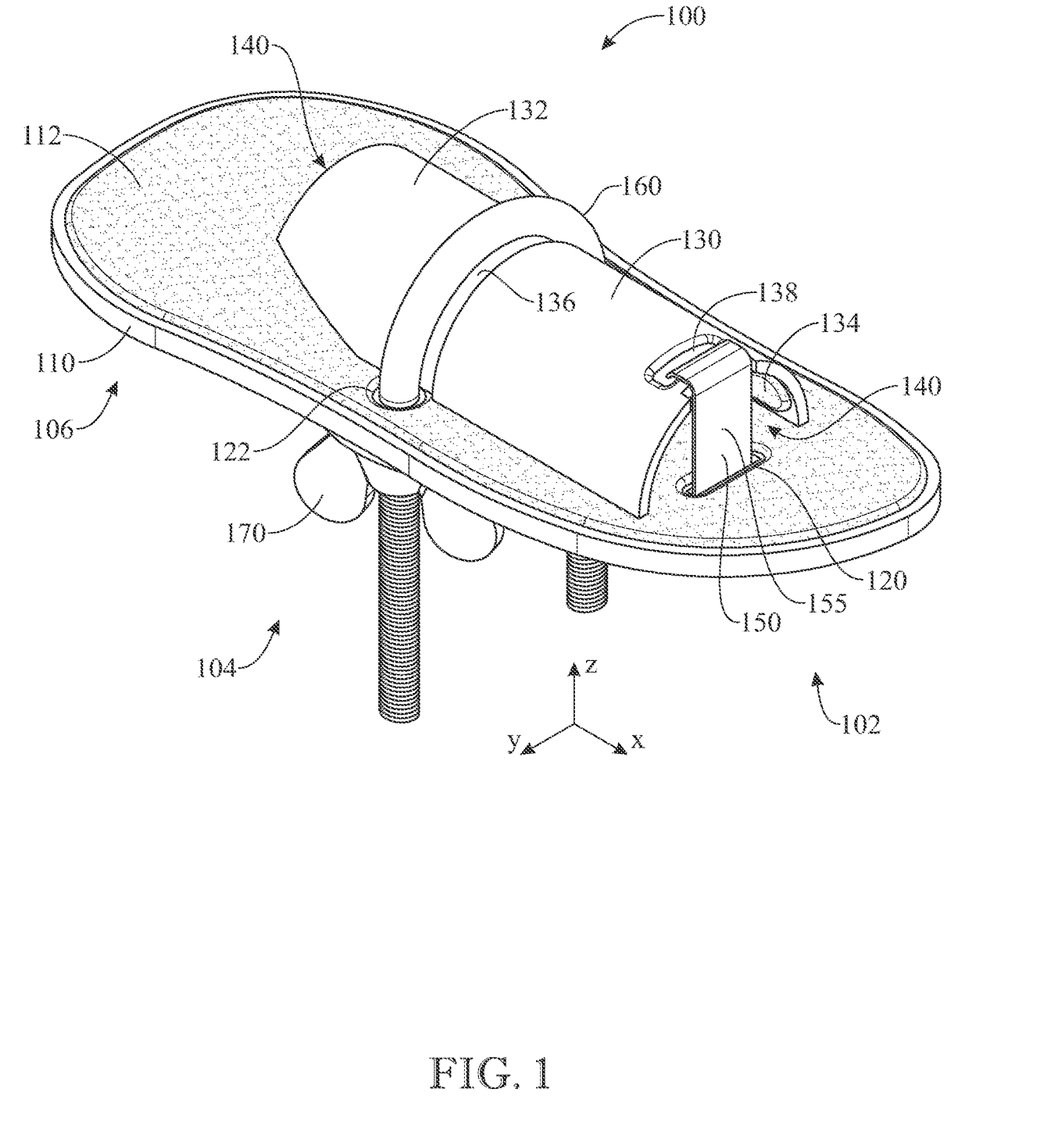
FIG. 1 illustrates a top, front or distal isometric view of a finger straightening device in an assembled state, in accordance with a first embodiment of the present specification.
Figure 2:
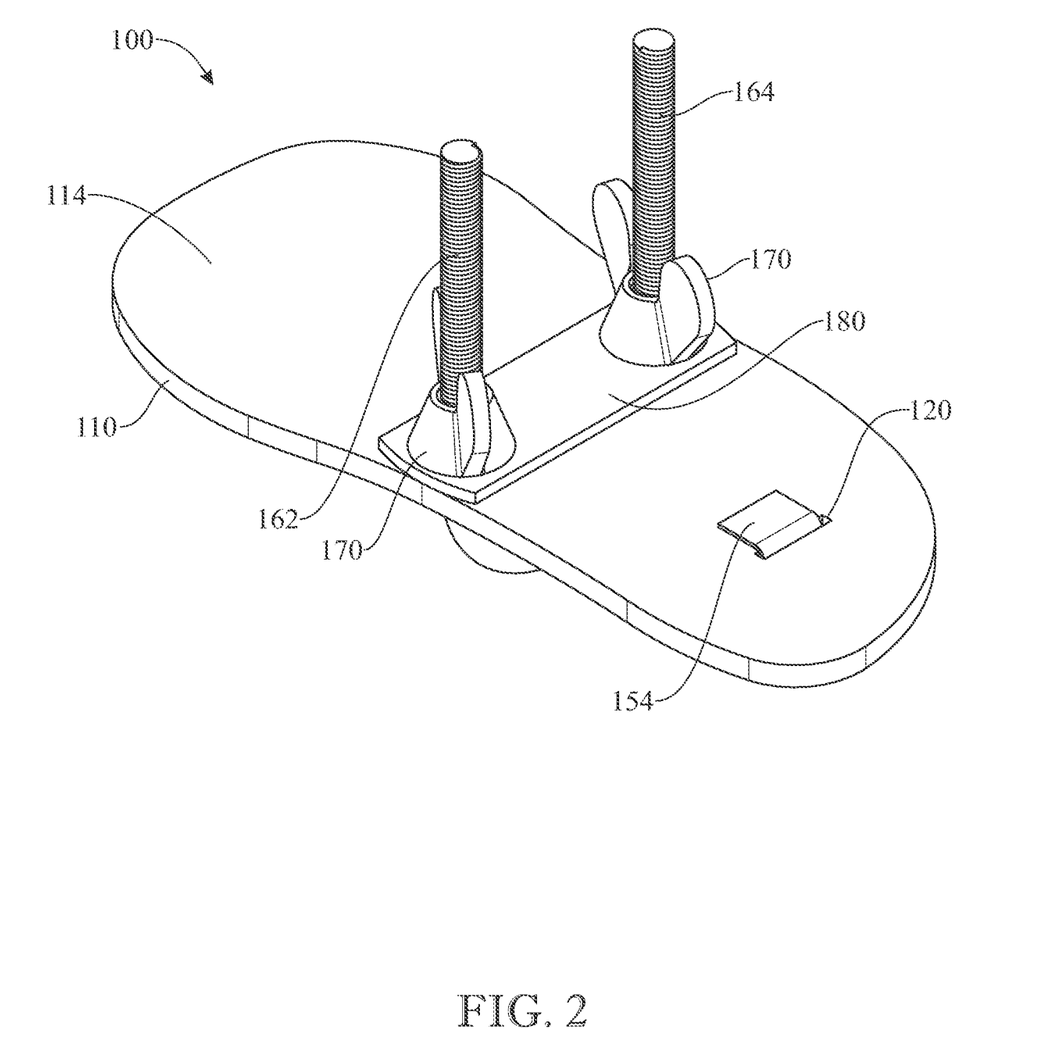
FIG. 2 illustrates a bottom, front or distal isometric view of the finger straightening device in an assembled state, in accordance with the first embodiment of the present specification.
Figure 3:
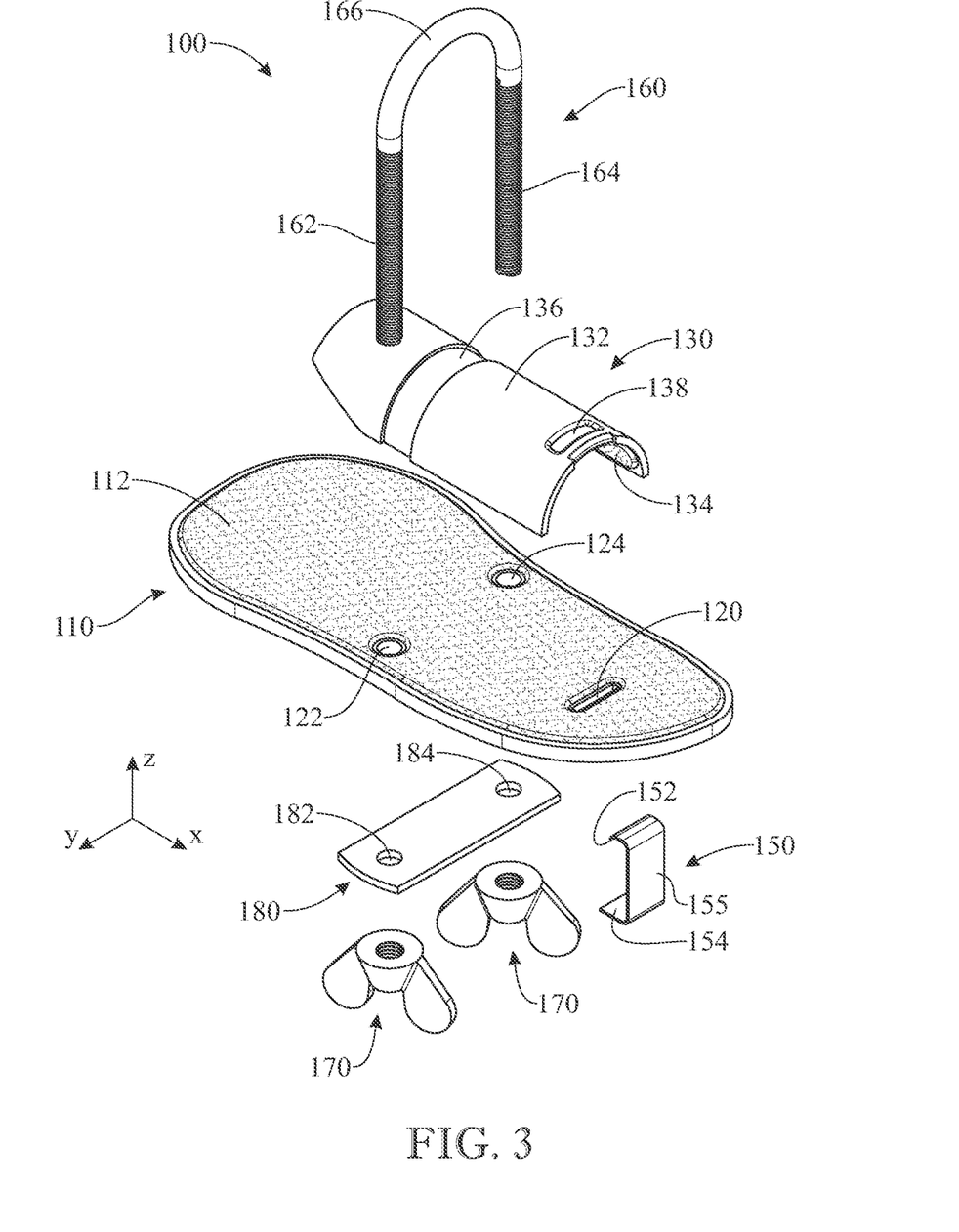
FIG. 3 illustrates an exploded, top distal isometric view of the finger straightening device, in accordance with the first embodiment of the present specification.

Referring initially to FIGS. 1-3, an isometric view of a finger straightening device is illustrated in accordance with a first embodiment of the present disclosure. The illustration of FIG. 1 shows a top, front isometric view of the finger straightening device 100 while FIG. 2 illustrates a bottom, front isometric view of the finger straightening device 100, the finger straightening device being in assembled state in both FIGS. 1 and 2. The illustration of FIG. 3 shows an exploded, top front isometric view of the finger straightening device 100.

The finger straightening device 100 comprises a base 110 that provides a resting area for a user to place a finger thereon. The base 110 comprises a top surface 112 (FIG. 1) and a bottom surface 114 (FIG. 2), the top surface 112 forming a resting area for a user to place a finger thereon. The base 110 may be formed of a suitable material that allows a finger of a user to be properly placed thereon. In some examples, the top surface 112 of the base 110 is a smooth surface so that a user placing the finger thereon does not feel any discomfort. In some examples, the top surface 112 of the base 110 may be covered with a layer of soft material to provide comfort to a finger of the user resting thereon. The layer of soft material may be a material having elastic properties, such as cloth and foam of various types.

The finger straightening device 100 further comprises a plurality of apertures formed in the top surface 112 and bottom surface 114 of the base 110. In the illustrated embodiment, as best shown in FIG. 3, the plurality of apertures includes a first aperture 120, a second aperture 122, and a third aperture 124. The second and third apertures 122, 124 may have similar dimensions and/or form factors so as to allow engagement with a common securing means, as will be described in detail further below. The first aperture 120 may have different dimensions as compared to the dimensions of the second and third aperture 122, 124 so as to allow engagement with a different securing means, as will be described further below.

With continued reference to FIG. 3, the finger straightening device 100 further comprises a cover 130 having an outer surface 132, and an inner surface 134 opposing to the outer surface 132. The cover 130 is configured to be adjustably coupled to the base 110 by means of one or more securing means. When coupled to one another, the cover 130 and the base 110 define a cavity 140 for a user to insert a finger therein. The cavity 140 may be elongated along a front-to-back or distal-to-proximal, longitudinal direction x, as shown. The cover 130 further comprises a groove 136 formed on the outer surface 132 and a cavity 138, which may be a through-hole or a recess, the cavity 138 extending between the outer surface 132 and the inner surface 134; for instance, in the present embodiment, the cavity 138 is a recess or groove which extends from the outer surface 132 towards the inner surface 134. In the present embodiment, the cavity 138 is generally elongated along a transverse direction y which is generally perpendicular to the longitudinal direction x. Each of the groove 136 and the cavity 138 allow the cover 130 to be adjustably coupled to the base 110. The inner surface 134 of the cover 130 is configured to apply a pressure on a finger inserted in the cavity 140, for instance, when the cover 130 is coupled to the base 110 by one or more securing elements. In some examples, the inner surface 134 may include a layer of soft material, such as materials with elastic properties, so as to not be uncomfortable for a user having a finger in the cavity 140.

In the illustrated embodiment, the finger straightening device 100 comprises a front or distal portion 102, a central portion 104, and a rear or proximal portion 106. As can be seen in FIGS. 1-3, the first aperture 120 is at the distal portion 102, and the cover 130 is coupled to the base 110 such that the cavity 138 is arranged distally of the groove 136, and the cavity 138 is at the distal portion 102 and the groove 136 is at the central portion 104. A user desiring to use the finger straightening device 100 inserts a finger into the cavity 140 formed between the base 110 and the cover 130 from the proximal portion 106 of the finger straightening device 100.

With reference to FIGS. 1 and 3, the finger straightening device 100 further comprises a first securing element 150 configured to adjustably couple the base 110 with the cover 130. In some embodiments, such as the present embodiment, the first securing element 150 couples the base 110 and the cover 130 by engaging with the first aperture 120 of the base 110 and the cavity 138 of the cover 130. In the illustrated embodiment, the first securing element 150 includes a first curved end 152 in engagement with the cavity 138 and a second curved end 154 in engagement with the first aperture 120, thereby coupling the base 110 with the cover 130. In some examples, the first securing element 150 is configured to allow at least some movement of the cover 130 with respect to the base 110, thus adjustably coupling the base 110 and the cover 130. A connecting portion 155 may extend from, and interconnect, the first curved end 152 to the second curved end 154. The first and second curved ends 152 and 154 and the connecting portion 155 may form a C-shaped arrangement, as best shown in FIG. 3.

In the illustrated embodiment, the first securing element 150 is in the form of a clip having a first and second curved ends 152, 154. As mentioned heretofore, the clip may be C-shaped. The first securing element 150 may be formed of a suitable material such as stainless steel to provide a secure, adjustable, and long lasting coupling of the base 110 with the cover 130.

The finger straightening device 100 further comprises a second securing element 160 configured to adjustably couple the base 110 with the cover 130. In particular, the second securing element 160 couples the base 110 and the cover 130 by engaging with the second and third apertures 122, 124 of the base 110 and with the groove 136 of the cover 130. The second securing element 160 acts as a common securing element that engages with both the second and third apertures 122, 124. The second securing element 160 includes a U-shaped bracket 161 having a first leg 162, a second leg 164, and a curved central segment 166 extending between the first leg 162 and the second leg 164. The curved central segment 166 and first and second legs 162 and 164 form a U-shaped arrangement, as shown. The curved central segment 166 may generally conform to the arcuate, groove 136 of the cover 130, as shown, allowing to maximize an abutment of the central segment 166 on the groove 136 when using the finger straightening device 100.

As seen in FIG. 3, the first leg 162 and the second leg 164 are threaded at an external surface thereof so as to couple with corresponding threaded fasteners, as will be described further below. When assembled to the base 110, the first leg 162 and the second leg 164 extend from the bottom surface 114 of the base 110, through the second and third apertures 122, 124 respectively, as can be seen in FIG. 2. The first leg 162 is adapted to pass through the second aperture 122 and the second leg 164 is adapted to pass through the third aperture 124. The length or extent of the first and second legs 162, 164 extending from the bottom surface 114 is adjustable by the user, thereby allowing to adjust a volume of cavity 140 between the base 110 and the cover 130, and consequently, an amount of force being applied on a finger inserted within the cavity 140, as will be described further below. Further, in the assembled state of the finger straightening device 100, the central segment 166 of the U-shaped bracket 161 is positioned within the groove 136 of the cover 130, as can be seen in FIG. 1. It is appreciated that the central segment 166 is not fixedly positioned within the groove 136 and the central segment 166 may be shifted out of the groove 136, for instance, when a user is inserting a finger into the cavity 140. In some embodiments, such as the present embodiment, the central segment 166, groove 136, and cover 130 may be generally arcuate to conform to an outer (upper) surface of a finger inserted through the cavity 140.

With continued reference to FIGS. 1-3, the second securing element 160 further includes a pair of fasteners 170 configured to couple with the first and second legs 162, 164 of the U-shaped bracket 161. Each of the fasteners 170 comprises an internally threaded surface that threadingly engages with the corresponding threaded surface of the first and second legs 162, 164, thereby forming an adjustable coupling arrangement between the U-shaped bracket 161 and the fasteners 170. In the illustrated embodiment, the fasteners 170 are wing nuts having an internally threaded surface. It is appreciated that, in different embodiments, the fasteners 170 are not limited to wing nuts and may be any other form of a threaded element that engages with the threaded surfaces of the first and second legs 162, 164.

The finger straightening device 100 further comprises a plate 180 comprising first and second through openings or passages 182 and 184 corresponding to, and configured to align with, the second and third apertures 122 and 124 of the plate 110 and the first and second legs 162 and 164 of the U-shaped bracket 161, respectively. The plate 180 is configured to be positioned between the bottom side 114 and the corresponding fasteners 170, and to extend from and interconnect the first and second legs 162 and 164, laterally stabilizing the first and second legs 162, 164 and contributing to improve the coupling hold between the first and second legs 162, 164 and the corresponding fasteners 170. In preferred embodiments, the plate 180 may be generally rigid.

The illustrations of FIGS. 1 and 2 show the cover 130 coupled to the base 110 by the first securing element 150 and the second securing element 160. The first securing element 150 is in engagement with the cavity 138 of the cover 130 and with the first aperture 120 formed in the base 110. The first and second legs 162, 164 are in engagement with the fasteners 170 while the central segment 166 is positioned within the groove 136. The coupling between the base 110 and the cover 130 is adjustable, in that, the first securing element 150 and second securing element 160 allow at least some movement of the cover 130 with respect to the base 110. The cavity 140 defined by the base 110 and the cover 130 allows a user to insert a finger therein from an end corresponding to the proximal portion 106 of the device.

The engagement of the fasteners 170 with the first and second legs 162, 164 can be seen more clearly in FIG. 2. The plate 180 abuts the bottom surface 114 of the base 110 and facilitates a secure engagement between the first and second legs 162, 164 and the corresponding fasteners 170. Due to the relatively large length of the threaded portion or threads on the exterior of the legs 162, 164 relative to the threaded interior of the fasteners 170, the fasteners 170 can be threaded to the legs 162, 164 at adjustable lengths or extents, the extent determining the volume of the cavity 140 between the base 110 and the cover 130, as will be described further below.

Figure 4:
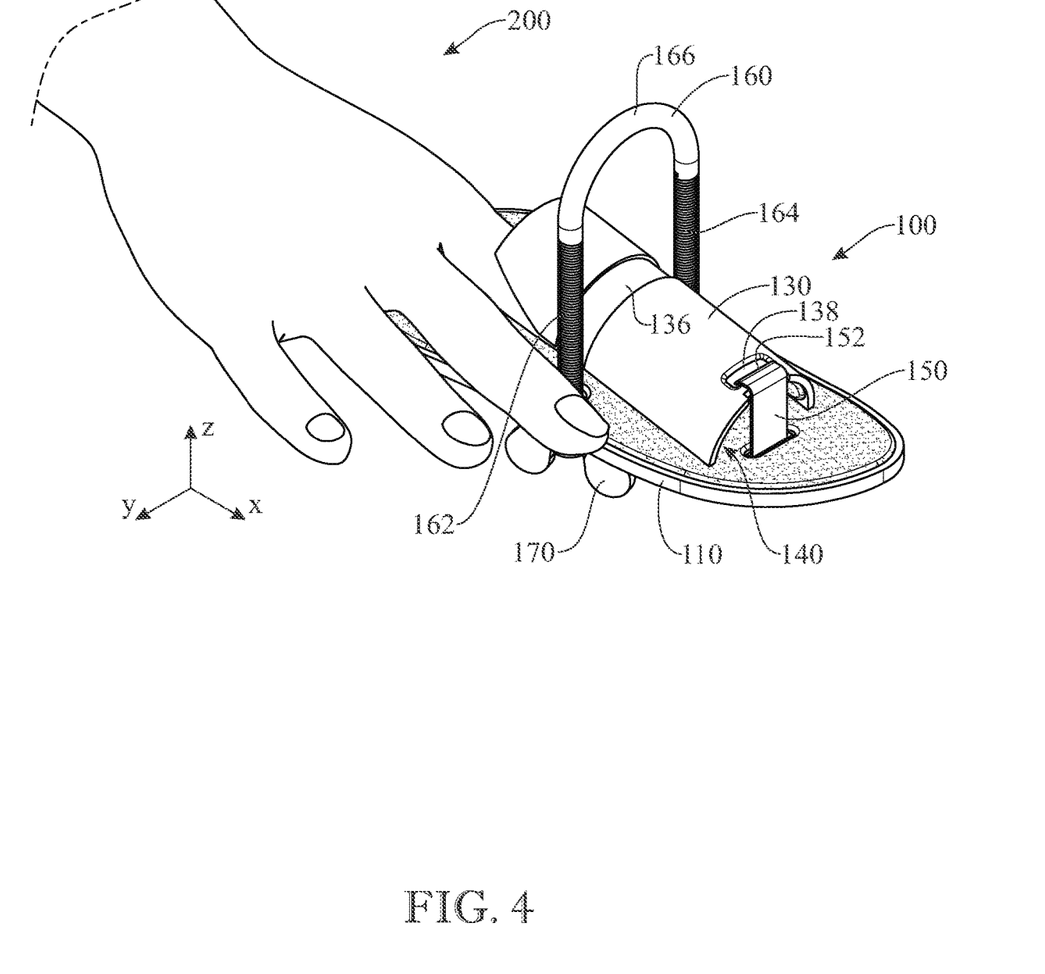
FIG. 4 illustrates a top, front or distal isometric view of the finger straightening device with a user inserting a finger at an initial stage, in accordance with the first embodiment of the present specification.

Reference is now made to FIG. 4, which illustrates the finger straightening device 100 when a user 200 is initially using the device by inserting a finger into the finger straightening device 100. The fasteners 170 are in engagement with the first and second legs 162, 164, the fasteners 170 being rotatable to adjust the extent of engagement, i.e., to loosen or tighten the engagement between the fasteners 170 and the first and second legs 162, 164. The fasteners 170 can be rotated in one direction to tighten the engagement, and in an opposite, second direction to loosen the engagement. The threaded surface of the first and second legs 162, 164 is of sufficient length to allow multiple positions of the fasteners 170 on the first and second legs 162, 164 by rotation of the fasteners 170, thereby allowing different extent of engagement between the fasteners 170 on the first and second legs 162, 164 as mentioned heretofore.

As seen in FIG. 4, the fasteners 170 have been rotated so as to loosen the extent of engagement with each of the first and second legs 162, 164. The U-shaped bracket 161 can now be moved to adjust the coupling between the base 110 and the cover 130. Thus, the coupling between the base 110 and the cover 130 is dependent on the extent of engagement between the fasteners 170 and the first and second legs 162, 164, i.e., on the position of the fasteners 170 on the corresponding legs 162, 164.

In FIG. 4, the position of the fasteners 170 on the corresponding legs 162, 164 is relatively close to the respective bottom or free ends of the legs 162, 164 such that a majority of first and second legs 162, 164 is free to be moved through the second and third apertures 122, 124. This allows the central segment 166 to be shifted out of the groove 136 and away from the base 110; consequently, the cover 130 is free to be adjusted with respect to the base 110. The adjustment of the cover 130 with respect to the base 110, and more specifically, towards or away from the base 110, facilitates varying the volume of the cavity 140 available for a user to insert a finger into, in that, the more the cover 130 is moved away from the base 110, the more the volume of the cavity 140 increases, providing a greater space for a user to insert a finger.

As can be seen in FIG. 4, the second securing element 160 is adjustably coupling the cover 130 with the base 110, allowing movement of the cover 130 with respect to the base 110. In some embodiments, such as the present embodiment, the coupling between the first securing element 150 and the cover 130, and more specifically, between the first curved end 152 and the cavity 138, may define a pivot point for the cover 130 to pivot relative to the base 110 when adjusting the separation of the cover 130 and the base 110 to enlarge or reduce the cavity 140. The pivoting of the cover 130 may take place about a rotation axis arranged generally in the transverse direction y and defined by the first curved end 152 being received inside the generally transverse, elongated cavity 138. A user 200 intending to initially insert a finger into the finger straightening device 100 may raise (pivot) the cover 130 upward and away from the base 110 to create a sufficient space within the cavity 140 to comfortably insert the finger without any restriction. According to the above mentioned configuration, users would not face any difficulty in inserting a finger into the cavity 140 of the finger straightening device 100 since the volume of the cavity 140 can be adjusted by means of the adjustable coupling between the cover 130 and the base 110 to accommodate fingers of different sizes and thickness. Furthermore, maintaining the cover 130 pivotably coupled to the base 110 during adjustment of the size of the cavity 140 may facilitate carrying out said adjustment.

Figure 5:
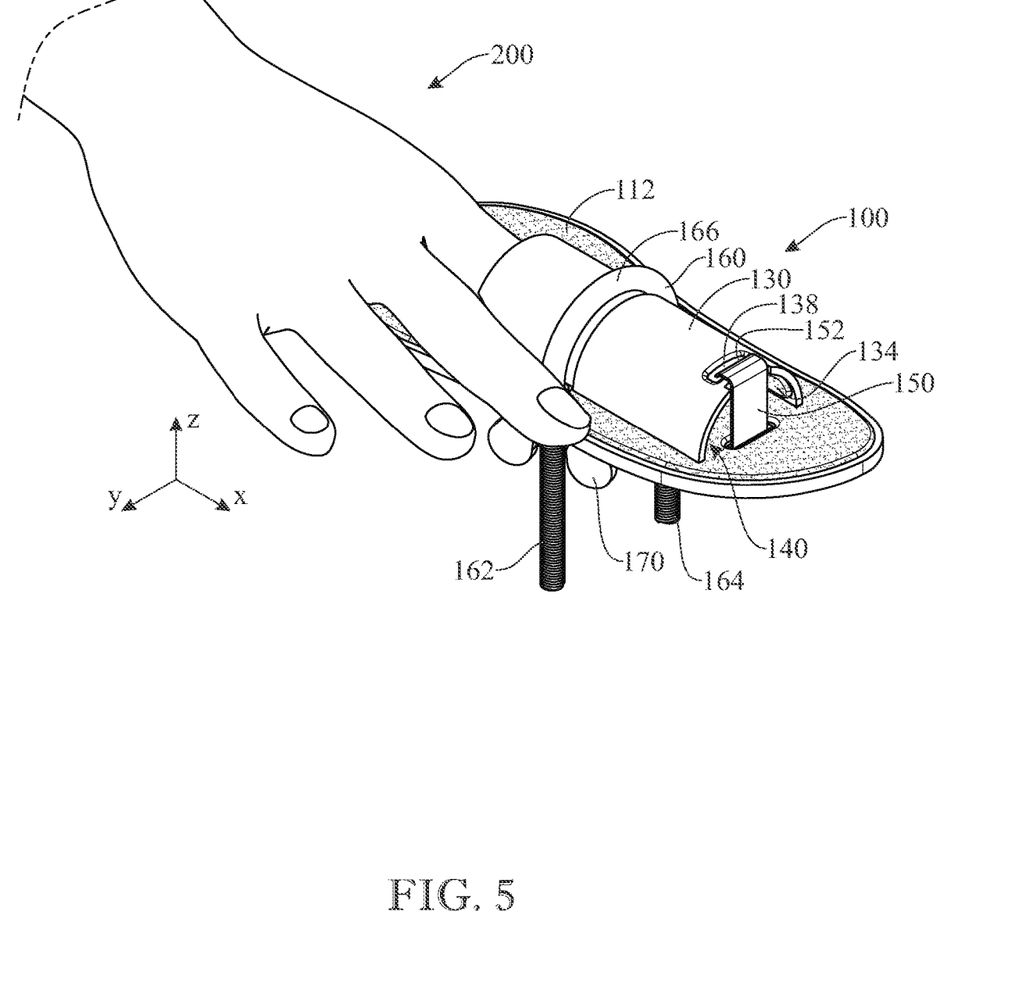
FIG. 5 illustrates a top, front or distal isometric view of the finger straightening device with a user using the device for straightening an inserted finger, in accordance with the first embodiment of the present specification.

Reference is now made to FIG. 5 that illustrates the finger straightening device 100 in use by a user 200. The user 200 inserts a finger into the cavity 140 formed between the base 110 and the cover 130. In particular, the finger of the user 200 rests on the top surface 112 of the base and is covered from above by the inner surface 134 of the cover 130. The cover 130 is coupled to the base 110 by the first securing element 150 and the second securing element 160, the second securing element 160 being in engagement with fasteners 170.

Based on position of the fasteners 170 on the first and second legs 162, 164, the coupling between the cover 130 and the base 110 can be adjusted. In one example, the user 200 manually rotates the fasteners 170 on the corresponding legs 162, 164 so as to adjust the positioning thereof. When a finger of the user 200 is inserted in the cavity 140, with the fasteners 170 sufficiently tightened, the inner surface 134 of the cover 130 applies pressure, i.e., a force on the inserted finger and presses the finger against the base 110. The force acting on the finger inserted in the cavity facilitates straightening of the inserted finger and relieves pain in the finger as the force introduces tension in the muscles and tendons surrounding the finger.

The position of the fasteners 170 on the corresponding legs 162, 164 defines the amount of pressure applied on the inserted finger by the cover 130, and more particularly, by the inner surface 134 of the cover 130 against the top surface 112 of the base 110. The fasteners can be rotated in one direction to tighten the coupling between the cover 130 and the base 110, and can be rotated in an opposite direction to loosen the coupling between the cover 130 and the base 110. The more the coupling between the cover 130 and the base 110 is tightened, the more the pressure is applied to the finger inserted in the cavity 140. With respect to the cavity 140, the more the coupling between the cover 130 and the base 110 is tightened, the less the volume of the cavity 140 into which a finger is inserted.

Accordingly, the user 200 can adjust the position of the fasteners 170 in engagement with the first and second legs 162, 164 by rotating the fasteners 170 in either the first direction or the second direction. The adjustment of the position of the fasteners 170 may depend on the pressure the user 200 desires to apply on the inserted finger. In case the user 200 desires to increase the pressure being applied to the inserted finger, the user 200 can rotate the fasteners 170 in the first direction, thereby tightening the coupling between the cover 130 and the base 110 and reducing the size of the cavity 140. This leads to a greater pressure being applied on the inserted finger with the inner surface 134 of the cover 130 applying a greater force on the inserted finger against the top surface 112 of the base 110.

In case the user feels discomfort with the amount of pressure being applied on the inserted finger, the user 200 can rotate the fasteners 170 in the second direction, thereby loosening the coupling between the cover 130 and the base 110. This leads to a lesser pressure being applied on the inserted finger with the inner surface 134 of the cover 130 applying a lesser force on the inserted finger against the top surface 112 of the base 110, or in other words, with the volume of the cavity 140 increasing to provide a greater space for accommodating the inserted finger.

Accordingly, the finger straightening device 100 allows a user to insert a finger into the cavity 140 of the finger straightening device 100 for straightening by means of a pressure applied thereto. A generally flat, rigid base 110 provides a straight support surface for the resting thereon of the finger, while the cover 130 may be adjustably positioned relative to the base 110 and the finger such that the cover 130 and base 110 adjustably press on the finger to ensure the finger remains fully resting on the base 110. The pressure to be applied on the inserted finger can be determined by the user himself/herself based on the amount of comfort or discomfort at any stage during use of the finger straightening device 100.

As an example, the user 200 initially sets the position of the fasteners 170 such that a first level of pressure is applied on the inserted finger. After a certain amount of time, the user 200 may desire to increase the pressure level, thereby changing the position of the fasteners such that a second, greater level of pressure is now applied on the inserted finger. Once the user wishes to remove the finger from the finger straightening device 100, the user can rotate the fasteners so as to loosen the coupling between the base 110 and the cover 130 to an extent where the finger can be easily taken out from the cavity 140.

Figure 6:
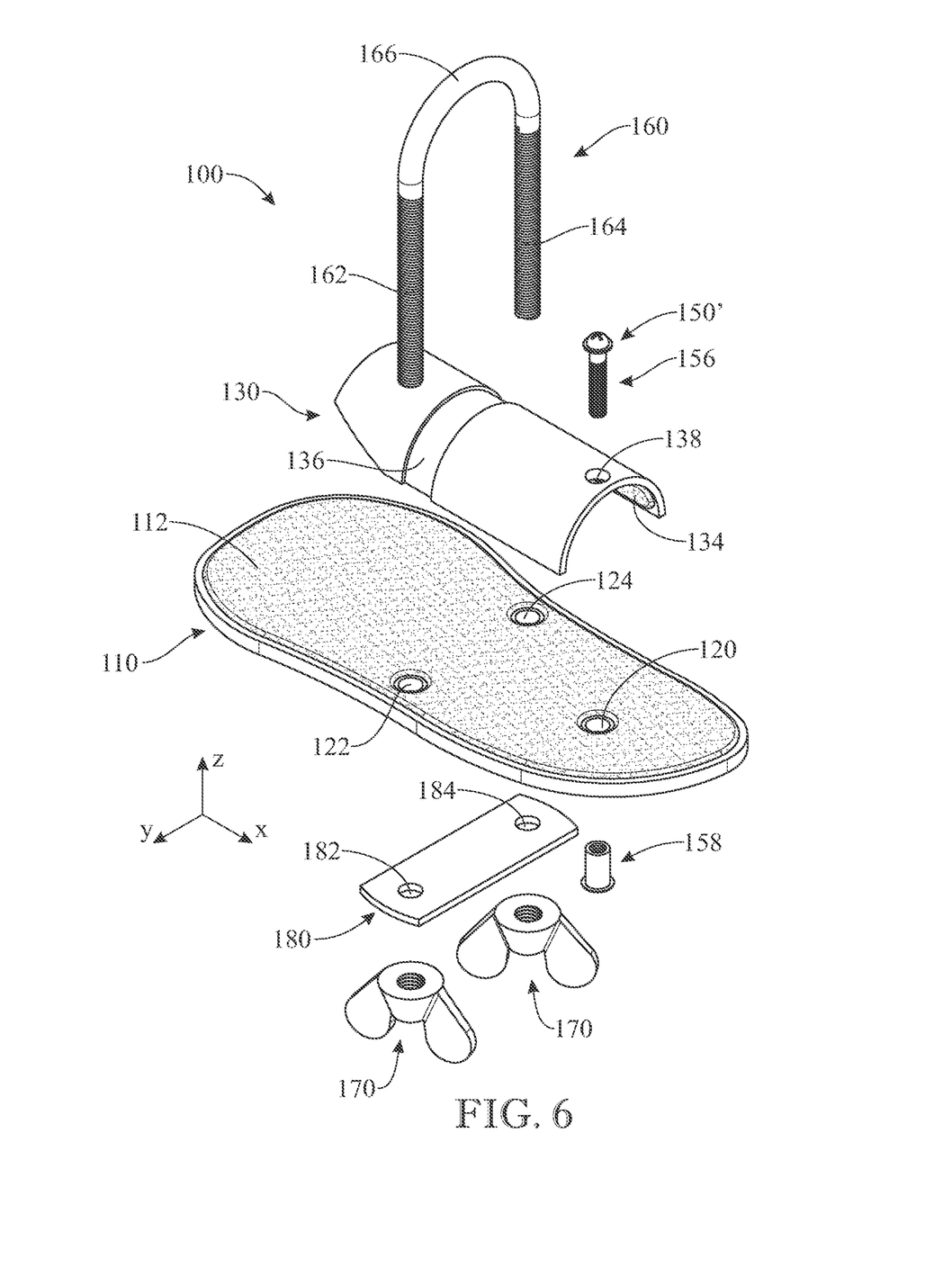
FIG. 6 illustrates an exploded, top distal isometric view of a finger straightening device, in accordance with a second embodiment of the present specification.
Figure 7:
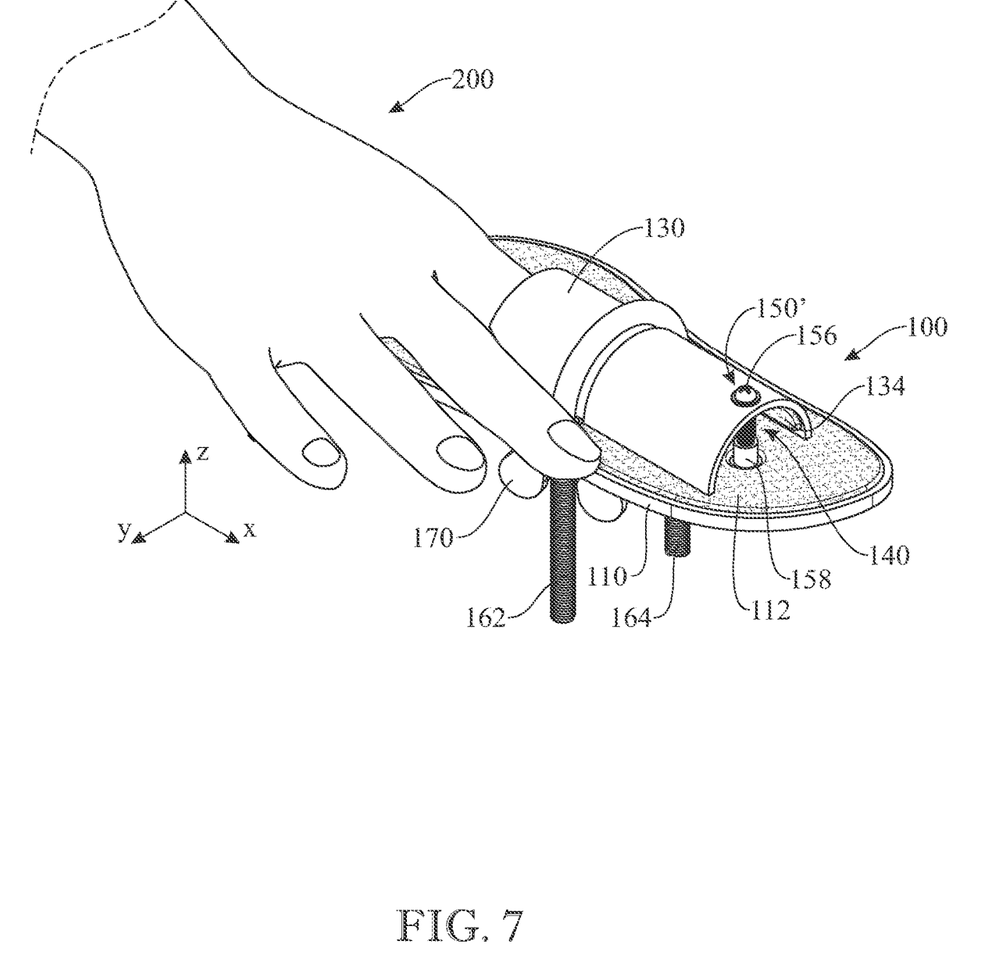
FIG. 7 illustrates a top, front or distal isometric view of the finger straightening device of FIG. 6 with a user using the device for straightening an inserted finger.

Referring now to FIGS. 6 and 7, an isometric view of the finger straightening device 100 is illustrated in accordance with a second embodiment of the present disclosure. The finger straightening device 100 illustrated in FIGS. 6 and 7 includes some identical elements as the finger straightening device of FIGS. 1-5, such as the base 110, the cover 130, the cavity 140, the U-shaped bracket 161, the fasteners 170, and the plate 180, the details of which are not repeated herein for the sake of brevity. In the embodiment illustrated in FIGS.

6-7, the finger straightening device 100 includes a first securing element 150' which is different than the first securing element 150 of the embodiment illustrated in FIGS. 1-5. As can be seen in FIGS. 6 and 7, the first securing element 150' includes a threaded bolt 156 and a cap nut 158.

The threaded bolt 156 is configured to pass through the first aperture 120 formed in the base 110 and the cavity 138 of the cover 130. The threaded bolt is configured to engage with the cap nut 158, the cap nut 158 having a corresponding inner thread or threaded surface. The arrangement of the bolt 156 and cap nut 158 allows coupling of the base 110 with the cover 130 in an adjustable manner such that the separation of the cover 130 and the base 110 may be adjusted. The arrangement of the bolt 156 and cap nut 158 allows a user to adjust the coupling of the base 110 and the cover 130 based on the amount of engagement between the bolt 156 and the cap nut 158.

The adjustment coupling between the base 110 and the cover 130 by means of the bolt 156 and the cap nut 158 allows users with different finger sizes and thickness to insert their finger for straightening and relieving pain, with the volume of the cavity 140 being adjustable by adjusting the engagement between the bolt 156 and cap nut 158. In case a user desires to tighten the coupling of the base 110 and the cover 130, the user can screw the bolt 156 further into the cap nut 158. Contrarily, in case a user desires to loosen the coupling of the base 110 and the cover 130, the user can screw the bolt 156 out of the cap nut 158.

In some embodiments, the cavity 138 of FIGS. 6 and 7 may be sufficiently larger than the shaft of the bolt 156 to enable a slight pivoting between the cover 130 and the base 110 about a transverse rotation axis when the bolt 156 and cap nut 158 are loosened. Furthermore, in some embodiments, the cover 130 may be slightly pivoted sideways, i.e. about a vertical rotation axis defined by the bolt 156, when the bolt 156 and cap but 158 are loosened, allowing to slightly adjust a horizontal orientation of the cover 130 relative to the base 130 in within a tolerance provided within the U-shaped bracket 161. It should be noted that 'vertical' is to be understood as arranged in a vertical direction z generally perpendicular to the longitudinal and transverse directions x and y, respectively.

The finger straightening device 100 illustrated in FIGS. 6 and 7 achieves the same purpose as the finger straightening device 100 illustrated in FIGS. 1-5, in that the finger straightening device 100 allows users to straighten their fingers for a predetermined amount of time by applying a pressure thereto, thereby relieving pain and discomfort from the fingers and the surrounding muscles and tendons.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A finger straightening device comprising:
    a base, comprising a top surface configured for the resting thereon of a finger along a proximal-to-distal, longitudinal direction of the base;
    a cover, positionable on the base to form a cavity between an inner surface of the cover and the top surface of the base, wherein the cavity is elongately formed and configured to receive the finger;
    a first securing element, configured to secure the cover to the base at a distal portion of the base; and
    a second securing element, configured to adjustably secure the cover to the base at a portion of the base arranged proximally to the distal portion; wherein
    the finger straightening device is configured to adopt an assembled configuration in which the cover is positioned on the base and the cavity is defined between the inner surface of the cover and the top surface of the base, and further in which the cover is secured to the base by the first and second securing elements, and the second securing element is adjusted to press the cover and base towards one another and thereby exert a pressure on the finger received within the cavity to maintain a position of the finger on the top surface of the base.

2. The finger straightening device of claim 1, wherein the top surface of the base is generally planar.

3. The finger straightening device of claim 1, wherein the inner surface of the cover is arcuate.

4. The finger straightening device of claim 1, wherein the second securing element comprises a U-shaped bracket and a pair of fasteners, the U-shaped bracket comprising a central segment and threaded, first and second legs extending from the central segment in a U-shaped arrangement, wherein the U-shaped bracket is attachable to the cover and base such that the central segment extends over and abuts against the cover and the first and second legs are inserted through respective first and second apertures formed in the base, and further wherein the pair of fasteners are adjustably threadable onto the first and second legs, respectively, at a bottom surface of the base opposite the top surface to selectively adjust a separation between the central segment and the top surface of the base.

5. The finger straightening device of claim 4, wherein an outer surface of the cover, opposite the inner surface, is configured to conform to an arcuate shape of the central segment of the U-shaped bracket.

6. The finger straightening device of claim 5, wherein the cover comprises an arcuate groove on the outer surface, and further wherein, in the assembled configuration of the finger straightening device, the central segment of the U-shaped bracket is received within the arcuate groove.

7. The finger straightening device of claim 4, wherein the finger straightening device is configured to adopt a loosened configuration in which the pair of fasteners are unthreaded from the first and second legs relative to the assembled configuration and the central segment of the U-shaped bracket is movable away from the top surface of the cover enabling a separation of the cover from the base at the distal portion of the base and facilitating insertion and removal of the finger into and from the cavity, respectively.

8. The finger straightening device of claim 7, wherein the cover is separable from the base at the distal portion of the base by pivoting relative to the base about a rotation axis defined by a pivot point formed by the cover and the first securing element.

9. The finger straightening device of claim 4, wherein each fastener of the pair of fasteners comprises a wing nut.

10. The finger straightening device of claim 4, wherein the second securing element further comprises a plate mountable between the bottom surface of the base and the pair of fasteners with the first and second legs of the U-shaped bracket extending through respective passages formed in the plate, the plate configured to abut against the bottom surface when the pair of fasteners are tightened and to maintain a separation between the first and second legs.

11. The finger straightening device of claim 1, wherein the cover is elongately formed.

12. The finger straightening device of claim 1, wherein the first securing element comprises a C-shaped clip connectable to a first aperture formed at the distal portion of the base and to a opening formed in the cover.

13. The finger straightening device of claim 12, wherein a connection between the C-shaped clip and the first aperture defines a pivot point between the cover and the first securing element, the pivot point enabling a pivotable movement of the cover relative to the base to selectively enlarge or shrink the cavity.

14. The finger straightening device of claim 13, wherein the finger straightening device is configured to adopt a loosened configuration in which the second securing element is adjusted to enable a separation of the cover from the base at the distal portion of the base and facilitate insertion and removal of the finger into and from the cavity, respectively.

15. The finger straightening device of claim 1, wherein the first securing element is configured to adjustably secure the cover to the base at the distal portion of the base, and further wherein, in the assembled configuration, the first securing element is adjusted to press the cover and base towards one another and thereby exert a pressure on the finger received within the cavity to maintain a position of the finger on the top surface of the base.

16. The finger straightening device of claim 15, wherein the first securing element comprises a threaded bolt and nut.

17. The finger straightening device of claim 1, wherein the first securing element is pivotably securable to the cover about a rotation axis arranged in a left-to-right, transverse direction generally perpendicular to the longitudinal direction.

18. The finger straightening device of claim 1, wherein the first securing element is pivotably securable to the cover about a rotation axis arranged in a vertical direction generally perpendicular to the longitudinal direction.

19. A finger straightening device comprising:
a base, comprising a top surface configured for the resting thereon of a finger along a proximal-to-distal, longitudinal direction of the base;
a cover, elongately formed and positionable on the base to form a cavity between an inner surface of the cover and the top surface of the base, wherein the cavity is elongately formed and configured to receive the finger;
a first securing element, configured to secure the cover to the base at a distal portion of the base; and
a second securing element, configured to adjustably secure the cover to the base at a portion of the base arranged proximally to the distal portion, the second securing element comprising a U-shaped bracket and a pair of fasteners, the U-shaped bracket comprising a central segment and threaded, first and second legs extending from the central segment in a U-shaped arrangement, wherein the U-shaped bracket is attachable to the cover and base such that the central segment extends over and abuts against the cover and the first and second legs are inserted through respective first and second apertures formed in the base, and further wherein the pair of fasteners are adjustably threadable onto the first and second legs, respectively, at a bottom surface of the base opposite the top surface to selectively adjust a separation between the central segment and the top surface of the base; wherein
the finger straightening device is configured to adopt an assembled configuration in which the cover is positioned on the base and the cavity is defined between the inner surface of the cover and the top surface of the base, and further in which the cover is secured to the base by the first and second securing elements, and the pair of fasteners are tightened onto the first and second legs to press the cover and base towards one another and thereby exert a pressure on the finger received within the cavity to maintain a position of the finger on the top surface of the base.

20. A finger straightening device comprising:
a base, comprising a generally planar top surface configured for the resting thereon of a finger along a proximal-to-distal, longitudinal direction of the base;
a cover, arcuately and elongately formed and positionable on the base to form a cavity between an inner surface of the cover and the top surface of the base, wherein the cavity is elongately formed and configured to receive the finger;
a first securing element, configured to secure the cover to the base at a distal portion of the base; and
a second securing element, configured to adjustably secure the cover to the base at a portion of the base arranged proximally to the distal portion, the second securing element comprising a U-shaped bracket and a pair of fasteners, the U-shaped bracket comprising a central segment and threaded, first and second legs extending from the central segment in a U-shaped arrangement, wherein the U-shaped bracket is attachable to the cover and base such that the central segment extends over, conforms to and abuts against the cover and the first and second legs are inserted through respective first and second apertures formed in the base, and further wherein the pair of fasteners are adjustably threadable onto the first and second legs, respectively, at a bottom surface of the base opposite the top surface to selectively adjust a separation between the central segment and the top surface of the base; wherein
the finger straightening device is configured to adopt an assembled configuration in which the cover is positioned on the base and the cavity is defined between the inner surface of the cover and the top surface of the base, and further in which the cover is secured to the base by the first and second securing elements, and the pair of fasteners are tightened onto the first and second legs to press the cover and base towards one another and thereby exert a pressure on the finger received within the cavity to maintain a position of the finger on the top surface of the base.

* * * * *